United States Patent [19]

Rodnyansky et al.

[11] 4,448,191

[45] May 15, 1984

[54] IMPLANTABLE CORRECTANT OF A SPINAL CURVATURE AND A METHOD FOR TREATMENT OF A SPINAL CURVATURE

[76] Inventors: Lazar I. Rodnyansky, ulitsa Karla Marxa, 133, kv. 47; Viktor K. Gupalov, ulitsa Gorkogo, 24, kv. 6, both of Krasnoyarsk, U.S.S.R.

[21] Appl. No.: 281,165

[22] Filed: Jul. 7, 1981

[51] Int. Cl.³ .......................... A61F 5/00; A61F 5/04
[52] U.S. Cl. .................................. 128/69; 128/92 R; 128/1 R
[58] Field of Search ................... 128/69, 75, 83, 84 R, 128/84 C, 92 R, 92 B, 92 E, 92 EA, 92 A, 1 R

[56] References Cited

U.S. PATENT DOCUMENTS

| | | | |
|---|---|---|---|
| 3,565,066 | 2/1971 | Roaf et al. | 128/69 |
| 3,693,616 | 9/1972 | Roaf et al. | 128/69 |
| 4,003,376 | 1/1977 | McKay et al. | 128/69 |
| 4,257,409 | 3/1981 | Bacal et al. | 128/69 |

*Primary Examiner*—C. Fred Rosenbaum
*Assistant Examiner*—C. W. Shedd
*Attorney, Agent, or Firm*—Fleit, Jacobson, Cohn & Price

[57] ABSTRACT

The implantable correctant of a spinal curvature of the present invention comprises a flat rod made from an elastic material and shaped as an arc, said rod being positioned on one side of the spinous processes with its convexity towards the convexity of the spine, and a device for fixing the rod on the spine, the device being adapted for such a fixation of the rod that the latter gets partially straightened to build up a force for the spine to rectify. The method for treatment of a spine curvature, according to the present invention, consists in that two incisions are made, one in the area of the thoracic spine and the other in the area of the lumbar spine on the convex side thereof, the spine is exposed at the incised places by being separated from the adjacent muscles, whereupon the rod is inserted into the incision in the area of the lumbar spine and pushed, towards the incision in the area of the thoracic spine, using the enclosed technique, lengthwise the spine while separating the surrounding soft tissues, after which the rod is positioned with its convexity towards the convexity of the spine and retained on the latter by the fixation device; this done the operative wounds are stitched by applying the layer by layer technique.

20 Claims, 11 Drawing Figures

IMPLANTABLE CORRECTANT OF A SPINAL CURVATURE AND A METHOD FOR TREATMENT OF A SPINAL CURVATURE

FIELD OF APPLICATION

This invention relates to surgical methods of treatment of spinal curvature and is concerned more specifically with implantable spinal curvature correctants and with methods for treatment of spinal curvature with the help of said correctants.

The invention is applicable for treatment of progressive forms of scoliosis involving the angle of curvature amounting to 50° according to Cobb. It can also be applied for treating kyphoscoliosis, juvenile kyphosis, Calvé disease, Kümmell's traumatic spondylitis, fresh and inveterate fractures of the spine accompanied by kyphotic deformation, as well as the cases of scoliotic deformation with the angle of curvature exceeding 50° according to Cobb.

BACKGROUND OF THE INVENTION

Clinical evidence in the USSR and abroad estimates the incidence of scoliotic disease in children of different ages to be from 4 to 6 percent on the average.

Scoliotic disease can be treated by conservative and surgical methods.

The now-existing conservative methods of treatment, such as therapeutic physical training, physiotherapy, correcting jackets prove to be efficacious not at all times, which necessitates searching for more perfect and reliable surgical methods of treatment. Thus, at least one child per every 1.5 thousand children needs surgical treatment. Therefore, many orthopedic specialists in leading countries of the world are now engaged in improving the now-existing surgical methods of treating scoliosis and kyphosis and in searching for new and more efficacious and economic ones.

Surgical treatment of scoliosis and kyphosis involves application of a great many diverse metallic structures and appliances for correcting the curvature of the spine and stabilizing the latter, which are implanted into the body of a patient either completely or partially.

Modern methods of surgical treatment applied for correcting spinal curvature, in particular, scoliosis incorporate as a rule two principal stages. At the first stage a fairly complicated and prolonged surgical intervention is carried out in order to rectify the spine, wherein the spine is mobilized by resecting the ribs and the transverse and spinous processes, dissecting the trunk erector muscles and both of the psoas muscles, whereupon the spine is rectified and fixed in that position with the aid of implantable correctants, straight rigid rods being most commonly used as such correctants and made fast on the bony structures of the spine. The second stage of the operation is in fact spondylosyndesis, that is, uniting of the vertebrae by virtue of osteoplasty.

Known in the present state of the art are some devices and appliances for stabilizing and correcting the spine by virtue of exertion developed thereby and applied lengthwise the spine, e.g., Harrington's distractor (cf. Harrington P. R. "Treatment of scoliosis. Correction and internal fixation by spine instrumentation". The Journal of Bone and Joint Surgery, vol. 44-A, No. 4, 1962, pp. 591–610).

The distractor comprises a straight rigid metallic rod provided with a hook at each end for the rod to fix on the spine. One of the rod ends has a thread in the form of cones for the hook to lock in a desired position.

A surgical operation for implanting the aforesaid rod occurs as follows. An incision is made lengthwise the spine to expose spinal bony formations, i.e., spinous and transverse processes, vertebral arches on both sides of the spine, viz, the convex and concave ones. Then holes are made between the arches of adjacent neutral unaffected vertebrae of the thoracic and lumbar spine to receive a respective hook, whereupon the rod and hooks are so positioned that the rod end provided with cones be situated in the superior portion of the trunk.

The rod is positioned on the concave side of the spine and fixed in place, using the hooks, by the arches or transverse processes of the vertebrae above and below the vertex of a spinal curvature. Next while moving the top hook along the rod one must distract the spine lengthwise, thus eliminating its curvature, whereupon the hook is locked in position.

Once the spine has been rectified bone grafts are placed on both sides of the vertebral spinous processes for the purpose of spondylosyndesis, where the operative wound is stitched up using layer-by-layer technique. The process of spondylosyndesis occurs within subsequent 3 to 5 months.

However, such exertion directed lengthwise the spine results in that high forces must be applied for rectifying a spinal curvature which migh cause fracture of the vertebral bony structures at the places of fixation, traction of the spinal cord, deranged function of the pelvic organs, paresis and paralysis of the lower extremities.

Thus, complete rectification of the spine cannot be obtained by the afore-discussed method.

In order to attain a higher degree of straightening of the spine and at the same time to render destruction of the spinal bony formations less probable, provision is made for some methods of treating a curvature of the spine with the help of a correctant with a transverse brace (cf. Cotrel "Techniques nouvelles dans le traitement de la scoliose idiopathique". International Ortopedics, vol. 1, No. 4, 1978, pp. 247–265).

The aforesaid correctant comprises the Harrington's rod discussed above, which is set on one side of the spinous processes at the spine concavity, and an additional transverse brace made as a short plate with hooks for the transverse processes to catch, said plate being positioned at the vertex of the spinal curvature on the other side of the spinous processes and being drawn to the rod by virtue of a threaded joint.

However, the afore-discussed constructions of implantable correctants of the spinal curvature based on the principle of exertion applied lengthwise the spine, can be used only in children whose growth has been completed, whereas use of such constructions in children with uncompleted growth is unreasonable, inasmuch as the spine of the children elongates with their growth, and the correctants lose the correcting effect within a short period of time.

In addition, insofar as both the convex and the concave sides of the spine are subjected to distraction in the course of the spinal curvature rectifying, such a construction of implantable correctant fails to provide proper conditions for a more intense growth of osseous tissues on the concave side of the spine in order to stabilize the position of the spine attained during the curvature straightening process, by equalizing the size of the vertebral bony structures on the convex and concave sides of the spine.

Prior-art implantable correctants of a spinal curvature are known to provide for correction and stabilization of the spine by exertion applied thereto square relative to its longitudinal axis (cf., e.g., the journal "Orthopedics, Traumatology and Prosthetics", No. 4, 1969, pp. 22-32/in Russian/). These constructions are in fact straight rigid metallic plates having a number of holes to receive a plurality of hooks having threaded ends. The hooks are adapted to catch the arches or the vertebral transverse processes situated at the vertex of the spinal curvature on the side opposite to that of the plate, which is situated on the concave side of the spine. Then the threaded ends of the hooks are passed through the respective holes in the plate or engaged with the plate, and the nuts are drawn until the spine is brought up close to the plate. As a result, the plate, the spine and the hooks define a rigid structure.

However, the afore-mentioned constructional arrangement of implantable correctants of a spinal curvature as a straight rigid rod or plate fails to provide an adequate correcting effect on the spine within the postoperative treatment. Oftentimes a repeated operation has to be performed to restore a requires amount of correcting action, and additional pulling up of the spine with the hooks by drawing up the nuts.

One more implantable correctant of a spinal curvature (cf. I. Resina and A. Ferreira Alvez, "A technique of correction and internal fixation for scoliosis". The Journal of Bone and Joint Surgery, vol. 59-B, No. 2, May, 1977, pp. 159-165) is known to be an elastic metallic rod fitted on the convex side of the spine and fixed with a wire at several points along the length thereof to the bases of the spinous processes, wherein holes have been made beforehand. Thus, the spine is rectified by virtue of elastic forces developed by the rod.

However, such an elastic rod fails to perform hypercorrection of the spine, i.e., to deflect the line of arrangement of the spinous processes in the direction opposite to the initial spinal curvature in order to eliminate torsion of the vertebrae and provide more favourable conditions for equalizing the size of the vertebral bony structures on the convex and concave sides of the spine by retarding and promoting the growth of osseous tissue, respectively.

Fixation pieces of all the afore-mentioned implantable correctants of a spinal curvature are causative of bone atrophy at the spots of bone-to-metal contact. That is why these correctants cannot be applied as permanent internal fixation pieces for correction and stabilization of the spine and have to be withdrawn in a comparatively short lapse of time long before completion of the treatment process, which in turn necessitates osteoplastic fixation of the spine, viz, uniting of the vertebrae by vertue of osteoplasty (spondylosyndesis). However, the osteoplastic fixation fails to maintain the extent of correction attained.

In order to intensify the rectifying action of implantable metallic appliances and devices and reduce the loss of the amount of correction attained, surgeons are to preliminarily mobilize the spine by performing complicated surgery on soft tissues, the spine and the thoracic cavity, e.g., severing the long dorsal muscles; dissecting the trunk erector muscles and the psoas muscle; resection of the vertebral and costal bodies; resection of the spinous, transverse and articular processes of the vertebrae; dissecting the fibrous rings of the intervertebral disks at several levels followed by enucleation of said disks.

However, such complicated surgical interventions prove to be vitally dangerous due to their being causative of shocks and involving large loss of blood.

Moreover, such a method of treatment is inadequately efficient, i.e., the correction attained due to the surgery carried out is lost by about 30 to 45 percent soon after the operation, whereby repeated operations are necessitated.

Still one more implantable correctant of a spinal curvature (cf. USSR Inventor's Certificate No. 450,572 issued on Dec. 15, 1974, published on Nov. 25, 1974 in Bulletin No. 43) is known to have an arcuate shape and be positioned with its convex side towards the convexity of the spine lengthwise the spinous processes and made fast on the spine by means of a fixation device so that the correctant gets partially straightened to build up a force for the spine to rectify. The correctant comprises a plurality of arcuate plates, four or five such plates being placed on each side of the spinous processes so that the plates situated on one side of said processes are in a close contact with one another to form a spring. The spine fixation device is made as a number of wire coils with which the plates and the spine are brought together, said wire coils catching the vertebrae by their arches.

However, such a constructional arrangement of the implantable correctant of a spinal curvature requires that an operative procedure for implanting said correctant should involve extensive bilateral stripping of the spine from the surrounding muscles.

Securing the correctant plates to the vertebrae with wire coils is a fairly labour- and time-consuming part of the surgery involved.

This may inflict an extensive traumatic intervention resulting in large blood loss (1200 to 2000 ml per operation) and in a prolonged operating time (2 to 3 hours), whereby such operations become vitally dangerous. It should also be noted that bilateral exposure of the spine inflicts trauma upon those groups of muscles which must be retained intact for patient's rehabilitation by auxiliary therapy methods, e.g., by exercise therapy or physiotherapy. In addition, bilateral exposure of the spine causes more frequent complications on the part of the operative wound, such as suppuration, seromas and even paraplegia.

On completing the course of treatment the correctant must be withdrawn, for which purpose repeated operative procedures should be resorted to.

Besides, mutual slipping of the correctant plates and their rubbing against one another are often causative of metalosis accompanied by formation of sterile seromas.

High extent of traumatic lesion resulting from an operative procedure for fixing the correcting rod to the spine creates a psychological barrier to practical application of the method. At early stage of the spine curvature in a child it is difficult to persuade his/her parents to subject the child to such an extensive operative intervention. This leads to the situation in which, surgical treatment is resorted to only in an inextricable situation in the case of a grave form of the spinal curvature, that is, the due time of treatment when it is much more efficacious, is missed. To fix the implantable correctants to the vertebral bony structures with a plurality of wire fasteners is a labour-consuming procedure taking much time to carry out. To control the degree of twisting of the wire fasteners of the correcting rods proves to be practically impossible.

When overtwisted (to provide a stronger fixation) the wire is liable to break or destructs the vertebral bony structures, whereas undertwisting of the wire fasteners results in loosened rod-to-spine attachment. As a result, there might occur within the postoperative period some displacement of the rod relative to the spine, whereby the correction attained earlier becomes lost. This, in turn, necessitates a many-month (18 to 24) postoperative treatment course with the help of plaster-of-Paris and removable jackets, which restrains patients' active motility and imposes limitation upon application of means and measures of exercise therapy to attain rapid rehabilitation; hence, the use of wire for fixation of the spinal curvature correctant fails to develop forces high enough for a complete spine rectification.

Thus, an operative procedure for implanting the aforesaid correctant is a very complicated one due to its being causative of shocks and a large amount of blood loss and take much time to occur, which tells adversely on the results of treatment.

SUMMARY OF THE INVENTION

It is an object of the present invention to provide an implantable correctant of a spinal curvature featuring such a constructional arrangement that would be instrumental in attaining higher efficacy of treating the spinal curvature.

It is another object of the present invention to develop a method for treatment of a spinal curvature using the implantable correctant mentioned above, which would render the operative procedure less traumatic.

It is one more object of the present invention to provide a correctant fixation device which would be capable of reducing the load on the vertebral osseous formations.

Said object is accomplished due to the fact that an arc-shaped implantable correctant of a spinal curvature positioned with its convexity towards the convex side of the spine lengthwise the spinous processes thereof and held in place on the spine by means of a fixation device so as to provide partial straightening of the correctant to build up a force for the spine to rectify, according to the present invention, is made as a single flat rod situated on one side of the spinous processes.

In order to bring the rod to the spine by the enclosed technique, i.e., by pushing it through soft tissues, it is expedient that one end or both ends of the flat rod be tapered so that the side surface of the rod end facing the convexity thereof should be an extension of the rod surface, whereas on the rod concave side said side surface of the rod end should have a bevel to engage the rod surface.

In order to rectify the spine in the frontal plane it is favourable that the rod fixation device should comprise two combs located at the rod ends on the rod convex side and facing the rod with their teeth, and transverse braces equal in number with the combs, said braces being connected with one of their ends to the rod and with the other end, to a respective comb and being adapted to adjust the force of the spine rectification.

In order to straighten the spine in the sagittal plane it is also expedient that the rod fixation device should comprise one or two additional hooks held at the rod ends so that each of these can catch the arch of a respective vertebra.

In cases where the angle of a spinal curvature exceeds 50° according to Cobb, it is desirable that the rod fixation device should incorporate some additional combs equal in number with the main combs and interposed between the rod and the main combs with the teeth of each comb facing the teeth of a corresponding main comb, said additional combs being made fast on a respective transverse brace of the main comb.

In order to ensure the rod fixation procedure with various types of spinal curvatures, it is advantageous that longitudinal oblong holes should be made in the tapered ends of the rod, and that the rod fixation device should comprise screws fitted into said holes, whereas the transverse braces should be mounted on said screws pivotally round the rod.

In cases of high degrees of a spinal curvature it is also favourable that the rod fixation device should comprise an additional pair of combs situated in the middle portion of the rod on the convex surface thereof, and a transverse brace with its end held to the rod and carrying said combs with their teeth facing one another.

A method for treating a spinal curvature with the use of an implantable correctant made as a flat arc-shaped rod, according to the present invention, consists in that an incision as long as the rod is made lengthwise the spine on the convex side of its curvature, the vertebrae at the ends of the incision are exposed by being separated from the adjacent muscles, the rod is positioned with its convexity towards that of the spine and held with its ends to the spine using a fixation device so that the rod gets partially straightened to build up a force for the spine to rectify and partially deflect to the side opposite to the initial curvature, and to provide better conditions for equalizing the size of bony structures on the convex and concave sides of the spine; once the rod has been fixed on the spine the operative wound is stitched up applying the layer by layer technique.

A method for treating a spinal curvature with the use of an implantable correctant made as a flat arc-shaped rod, according to the present invention, consists in that two incisions are made, one in the area of the thoracic spine and the other in that of the lumbar spine, respectively for the rod ends to fix in place therein, the vertebrae at the places of incisions are exposed by being separated from the adjacent muscles, whereupon the rod is inserted into the incision in the area of the lumbar spine and pushed using the enclosed technique, lengthwise the spine while separating the soft tissues, towards the incision in the area of the thoracic spine, then the rod is positioned with its convexity towards that of the spine and retained with its ends on the spine using the fixation device so that the rod gets partially straightened to build up a force for the spine to rectify; this done the operative wounds are stitched up applying the layer by layer technique.

Such a constructional arrangement of an implantable correctant of a spinal curvature makes it possible to substantially reduce the extent of traumatic lesion inflicted by an operative procedure for implanting the aforesaid correctant, hasten such an operation and render more efficient the treatment of scoliosis and other spinal curvatures.

BRIEF DESCRIPTION OF THE DRAWINGS

Other objects and advantageous features of the present invention will be readily appreciated as the same becomes better understood by reference to the following detailed description of a specific embodiment thereof when considered in connection with the accompanying drawings, wherein.

DETAILED DESCRIPTION OF THE INVENTION

Reference being now directed to the accompanying drawings the implantable correctant of a spinal curvature is made as a single flat rod 1 (FIG. 1) shaped as an arc. The rod 1 is made from an elastic material, e.g., a titanium alloy and must be positioned on a spine 2 with its convexity towards that of the spine 2 lengthwise spinous processes 3 on one side of the spine 2 and be made fast on the latter with a fixation device so that the rod 1 gets partially straightened to build up a force for the spine 2 to rectify. In order to rectify the spine 2 featuring a curvature at an angle of from 45° to 50° according to Cobb, a force of from 400 to 600 N must be applied, while at an angle of the spine curvature exceeding 50° the required force may be over 1000 N. The length of the rod 1 usually ranges between 265 and 285 mm, the thickness, between 1.5 and 2 mm, the width, between 8 and 10 mm, the radius of curvature being 200 mm. The rod 1 is adapted for being pushed, using the enclosed technique through the soft tissues lengthwise the spine 2. With this aim in view both ends 4 of the flat rod 1 are tapered so that the side surface of the rod end 4 facing the rod convexity is an extension of the surface of the rod 1, while on the rod concave side said side surface of the rod end has a bevel to engage the rod surface.

Figure 1:
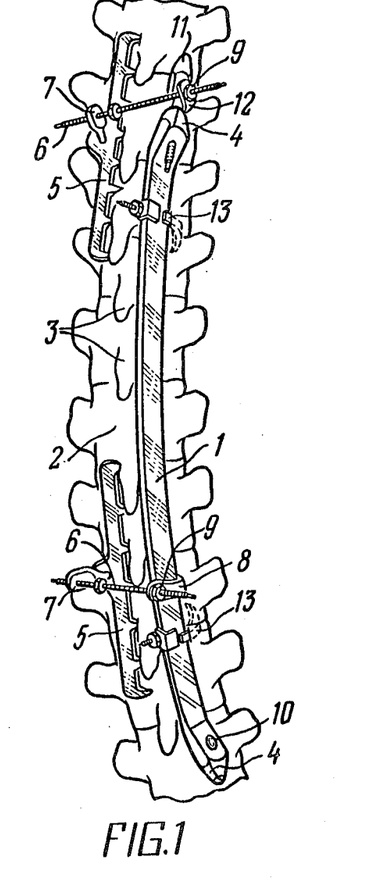
FIG. 1 is a general view of an implantable correctant of a spinal curvature when made fast on the spine, according to the present invention.

The device for fixing the rod on the spine 2 comprises two combs 5 having pointed teeth with which the spine 2 is fixed in the frontal plane. The combs 5 are located at the ends 4 of the rod 1 on its convex side with their teeth facing the rod 1, and are connected to the rod 1 by means of cross braces 6. One of the ends of each cross braces 6 carries a holder 7 of the comb 5, said holder being mounted on said cross braces through a threaded joint or nut, the other end of the cross brace 6 carrying a clamp 8 and having a thread which mounts a nut 9 adapted to adjust the force of rectification of the spine 2.

Longitudinal oblong holes 10 are made in the tapered ends 4 of the rod 1, one of said holes 10 accommodating a screw 11 having a tapered head with a rounded tip. This rod end 4 is the cranial one when the rod is fixed on the spine 2, and is made fast rigidly on the latter. The other end 4 of the rod 1 is the caudal one when the latter is fixed on the spine 2, and is movable lengthwise the spine in response to the child's growth. The rod 1 is positioned on one side of the spinous processes 3, while the combs 5 are situated on the other side of said processes. Thus, the combs 5 lock the spine 2 in the frontal plane. The cross brace 6 is held to the cranial rod end by means of a clamp 12, which with its recurvate end catches the screw 11 and is held in between the head of said screw and the tapered end 4 of the rod 1, whereby the cranial rod end is fixed rigidly in position. To render the caudal rod movable lengthwise the spine 2 the clamp 8 catches the rod 1. The cranial rod end may also be mounted by means of the clamp 8 which is so positioned as to thrust against the thickened taper portion of the end 4. In order to extend the rod 1 the hole 10 in the caudal end of the rod 1 may receive the screw 11, while the cross brace 6 of the comb 5 may be fastened by means of the clamp 12, which must be so positioned that a gap should be provided between its edge and the head of the screw 11 for the rod 1 to move lengthwise in response to the child's growth.

The length of the comb 5 is so selected that when mounted along the spine 2, the comb 5 can catch at least two spinous processes 3; as a rule the comb 5 is 85 mm long. The teeth of the comb 5 are pointed in order that they could pierce easily into the spinous processes 3. Usually the comb 5 has eight teeth, and they are spaced so apart that one or two teeth could pierce into each of the spinous processes 3 along which the comb 5 is situated.

Figure 2:
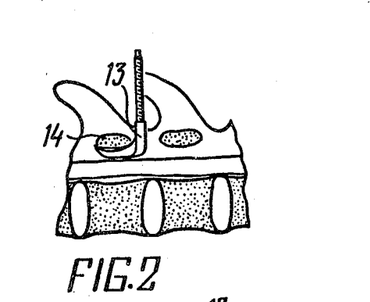
FIG. 2 is a longitudinal section view of a portion of the spine taken in the sagittal plane to show the hook catching the vertebral arch, according to the present invention.
Figure 4:
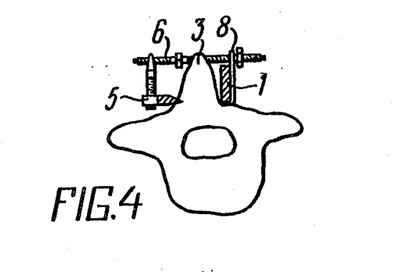
FIG. 4 is a cross-sectional view of the spine at the place of a comb positioning, according to the present invention.
Figure 5:
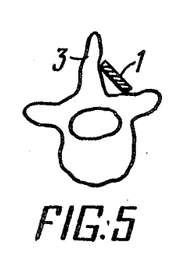
FIG. 5 is a cross-sectional view of the spine with the rod made fast thereon to illustrate the position of the rod with respect to spinal osseous formations in kyphoscoliosis, according to the present invention.
Figure 6:
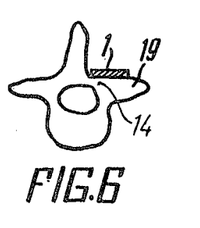
FIG. 6 is the same as in FIG. 5 in the case of kyphosis, according to the present invention.
Figure 7:
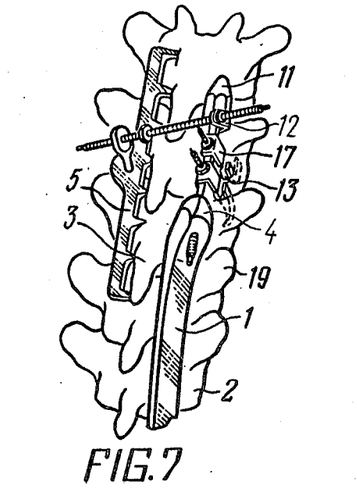
FIG. 7 is a version of the rod fastening on the spine in the case of scoliosis, according to the present invention.

In order to lock the spine 2 in the sagittal plane the device for fixation of the rod 1 comprises two hooks 13 held at the ends of said rod, each of said hooks being adapted to catch a vertebral arch 14 (FIGS. 2 and 3), thus fixing the rod 1 in position. The hook 13 has a slot 15 (FIG. 3) to suit the thickness of the rod 1, while its threaded shank 16 mounts a clamp 17 and a nut 18, whose rotation causes the clamp 17 to travel when the rod 1 is being fixed on the spine 2. In the case of scoliosis the rod 1 with its convexity faces the spinous processes 3 (FIG. 4), whereas in the case of kyphoscoliosis the rod 1 (FIG. 5) is turned with respect to the spinous processes 3. In the case of kyphosis the rod 1 (FIG. 6) with its convexity faces the arches of the vertebrae. In both of the latter cases the combs 5 and the hooks 13 are mounted on the screws 11 pivotally round the rod 1, while the spine 2 is fixed in the sagittal plane by the two hooks 13 (FIG. 7) facing oppositely and adapted to catch the arches of the adjacent vertebrae when fixing the rod 1 on the spine.

In cases of fractures of the spine 2 accompanied by kyphotic deformation the rods 1 are to be positioned as in the case of kyphosis, as will as in cases of Calve's and Kummell's diseases, the length of the rod 1 depending on the distance between extreme fractured vertebrae. The rods 1 are positioned in the cases of Calve's and Kummell's diseases on the longitudinal sides of the diseased vertebra.

Such a constructional arrangement of the device for fixing the rod 1 makes it possible to distribute the force rectifying the spine 2 between several vertebrae, to reduce load on each of the osseous formations thereof, to increase the force rectifying the spine 2 and to avoid destruction of the spinal bony structures.

Figure 8:
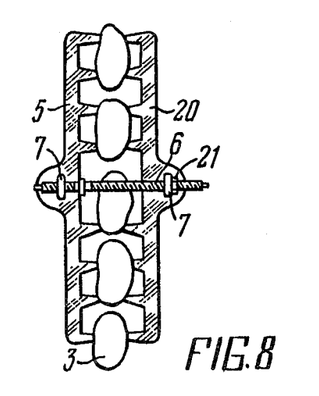
FIG. 8 shows a pair of combs adapted for rod fixation, each of said combs being arranged on either side of the spinous processes, according to the present invention.

In cases of higher degrees of curvature of the spine 2 a pair of the combs 5 are practicable to be used for fixing the rod 1. Such being the case the device for fixing the rod 1 comprises also additional combs 20 (FIG. 8) in a number to suit the number of the main combs 5, said additional combs having pointed teeth and each being interposed between the rod 1 and the main comb 5 with its teeth facing those of the main comb 5. The additional combs 20 are held to the cross brace 6 of the main comb 5. When fastening the rod 1 on the spine the additional combs 20 are situated on the same side of the spinous processes 3 as the rod 1, and are transversable along the cross brace 6 when a nut 21 is being rotated.

Figure 9:
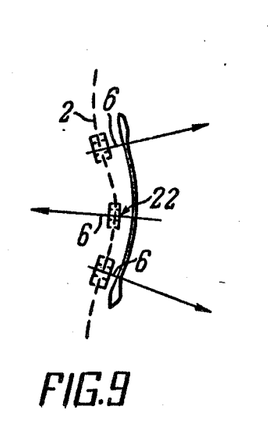
FIG. 9 is a schematic diagram of the rod-to-spine attachment with the use of three pairs of combs, according to the present invention.

With the angle of curvature of the spine equal to 50° or over according to Cobb it is expedient that an additional pair 22 (FIG. 9) of combs be provided at the vertex of the spinal curvature and that the cross brace 6 of said pair 22 be made fast on the rod 1 in the middle portion thereof. To provide more efficient treatment a preliminary rectification or straightening of the curvature of the spine 2 may be resorted to. To this aim special adpaters (not shown) are to be screwed onto the ends of the cross braces 6 to receive Kirschner's pins or kapron cords (shown with arrows for clarity), which are brought outwards laterally of the patient's body and fixed to the external correcting apparatus of any heretofore construction, e.g., LatypovAkberov's apparatus.

For passing the rod 1 in a closed manner two incisions 23 and 24 (FIG. 10) are to be made in the patient's body lengthwise the spine 2, whereupon the rod 1 is pushed through the soft tissues using a special handle 25 screwed into the hole 10 in caudal end 4 of the rod 1. To fix the rod 1 in position the nuts 9 (FIG. 11) are to be turned in until the spine 2 gets rectified.

The herein-disclosed implantable correctant of a spinal curvature is positioned on the spine to be rectified as follows. First of all the places of fixing the combs 5 are determined under the guidance of the preliminarily taken X-ray photos of the spine 2 (FIG. 10) in the frontal and sagittal planes, i.e., there are marked the places of the operative incisions 23 and 24. The surgical intervention is carred out under general anesthesia with the patient in the prone position. The curvatures of the spine 2 in the sagittal plane are rectified by placing rigid pads or bolsters under the stomach or chest.

Figure 10:
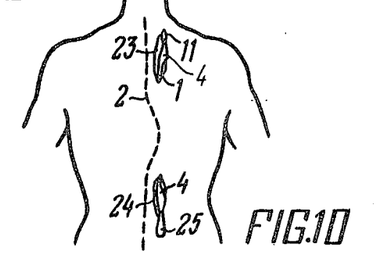
FIG. 10 shows a stage of an operative procedure for positioning the correcting rod before holding it to the spine (the latter being in a curved state), according to the present invention.
Figure 11:
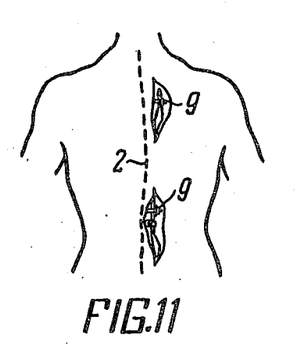
FIG. 11 is the same in FIG. 10 after the rod has been fixed in position on the spine (the latter in a rectified state), according to the present invention.

Then the incisions 23 and 24 are made in the areas of the thoracic and lumbar spines, respectively, said incisions being directed lengthwise the spinous processes 3 (FIG. 1) on the convex side of the curvature of the spine 2 (FIG. 10), whereupon the spine is exposed by separating the adjacent muscles. The length of each of the incisions 23, 24 must be within the length of the comb 5 (FIG. 1). Thereupon the hooks 13 are brought under the vertebral arches 14 (FIGS. 2, 3), one hook per the thoracic and the lumbar incisions 23, 24, respectively (FIG. 10).

Next the muscles are separated from the spinous processes 3 (FIG. 1) on the convexity of the spine 2 through the incisions 23 and 24, and the comb 5 is inserted into the incision 23, whereupon the cross brace 6 is screwed into the holder 7. In the case of low spinous processes 3 the cross brace 6 is situated above the processes 3, whereas in the case of high spinous processes the cross brace 6 is passed through the process 3 or through the interspinous space.

Figure 3:
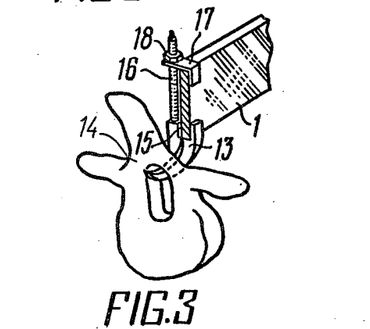
FIG. 3 is a cross-sectional view of a vertebra to illustrate the position of the hook and rod with respect to the vertebral arch, according to the present invention.

A next important stage of the operation is to position the rod 1. First the screw 11 and the handle 25 must be turned each into the respective hole 10 made in the tapered ends 4 (FIG. 10) of the rod 1. Then the correcting rod 1 is passed from the bottom incision 24 to the top incision 23, or vice versa. While so doing the head of the screw 11 separates the surrounding muscles in a dull (bloodless) manner. Having passed the rod 1 in the case of scoliosis, it is fitted into the slot 15 (FIGS. 3, 4) in the hook 13 under the cross brace 6 of the comb 5. Then the clamp 12 (FIG. 1) with the nut 9 is set onto the cross brace 6 of the comb 5, and the clamp 17 with the nut 18 is fitted onto the shank 16 (FIG. 3). Next the cranial end 4 of the rod 1 is fixed rigidly on the spine 2 by rotating the nut 9 (FIG. 1) and the nut 18 (FIG. 3) so that the rod 1 (FIG. 4) should be situated, in the case of scoliosis, in the sagittal plane, while the teeth of the comb 5 should pierce into the spinous processes 3 at their bases. The surplus of the shank 16 and the cross brace 6 are cut off with nippers.

The caudal end of the rod 1 is fixed in position in the lumbar incision 24 (FIG. 10) in the same way and sequence of steps as the cranial end. However, when turning in the nuts 9 and 18 one must take into account that the rod 1 should be free to slide upwards in the clamp 8 (FIG. 4) and the slot 15 of the hook 13 in response to the growth of the child patient. Besides, the clamp 8 and the hook 13 (FIG. 1) must be so mounted on the rod 1 that a distance be left to the rod end 4 at least equal to the amount by which the spine 2 of the child will be extended by the onset of puberty. Once the rod 1 has been fixed in place the spine 2 (FIG. 11) is rectified on the operating table, whereupon the operative incisions 23 and 24 are stitched up applying the layer by layer technique.

The rectifying action of the correcting rod on the spine 2 persists until the rod is withdrawn and is accompanied by a growth of the osseous formations of the spine 2 and the rectification of the latter due to more intense growth of the vertebrae on the concavity of the spine 2 and simultaneous inhibition of their growth on the spine convexity.

Once the patient's growth has terminated, the rod 1 (FIG. 1) is withdrawn in a closed manner. In this case, the bevelled surface of the tapered end 4 enables the rod 1 to be removed by bloodless separation of the surrounding soft tissues. If necessary, the rod 1 may take the function of an endoprothesis.

An operative procedure for positioning the rod 1 in the case of kyphoscoliosis occurs in the same sequence with the exception that, for the rod 1 (FIG. 5) to turn the clamps 12 (FIG. 7) of the combs 5 and the clamps 17 (FIG. 3) of the hooks 13 catch the screw fitted in the holes 10 which are made in both ends 4 of the rod 1. Two hooks 13 are made use of for higher rigidity of fixing the rod 1. The thus-positioned rod 1 exerts a rectifying effect on the sagittal and frontal curvature of the spine 2 at a time.

When the spine 2 features an angle of curvature of 50° and over according to Cobb, the rod is fixed in the spine 2 using three pairs 22 (FIG. 9) of the combs 5 and 20 situated at three levels of the spine, viz, thoracic, lumbar and at the vertex of the spinal curvature. The operative procedure is carried out as follows.

Three incisions are made respectively in the area of the thoracic and lumbar spines and at the vertex of the curvature of the spine 2, whereupon the hooks 13 (FIG. 7) are set in position as described hereinabove. Then the combs 5 and 20 are set in pairs on both sides of the spinous processes 3 (FIG. 8) so as to face each other with their teeth. The cross brace 6 is turned or introduced first into the holder 7 (FIG. 8) of the comb 20 located on the convexity of the spine 2, then into the holder 7 of the the comb 5 situated on the concavity of the spine 2. Next the nut 21 is rotated to bring the comb 20 towards the spinous processes 3 until the teeth of said comb pierce into the processes 3, whereupon the nut 9 (FIG. 1) is rotated to bring the comb 5 situated on the concavity of the spine 2, to the latter. Further procedure for fixation of the rod 1 occurs as described hereinbefore.

In cases of scoliosis involving a spine curvature angle within 70° according to Cobb when the correcting rod 1 still can be bent, some adapters are held to the cross braces 6 (FIG. 9), said adapters carrying pins or kapron cords (not shown) whose ends are brought outwards and held to the frame (not shown) adapted to exert progressive lateral rectifying effect on the curved spine 2. Once a required degree of correction has been attained the pins and adapters are removed.

In cases of scoliosis involving a spine curvature angle in excess of 70° according to Cobb when the correcting rod 1 cannot be bent as this results in destruction of the osseous formations of the spine 2, the operation is performed in two stages. First the pairs 22 (FIG. 9) of the combs 5, 20 and theh hooks 13 are positioned at three levels as described above, and preliminary straightening of the spine 2 is effected with the help of a frame-type apparatus of the heretofore known construction. At the second stage that follows the attaining of a required degree of mobility of the spine 2, the correcting rod 1 is implanted as described hereinbefore.

During operative procedures carried out for kyphotic deformation of the spine 2 and rod 1 is positioned in the frontal plane.

In fresh and inveterate fractures of the spine 2 accompanied by kyphotic deformation, the rod 1 is fixed to the spine 2 as in the case of kyphosis, but shorter rods are made use of.

CLINICAL TRIAL DATA

Surgical interventions for positioning an implanting correctant of a spinal curvature have been carried out in 15 patients aged from 7 to 16 who suffer from progressive forms of third-degree scoliosis of the thoracic and thoracolumbar spines, i.e., with an angle of curvature lying within 50° according to Cobb. In the elder children the rod 1 has been fixed to the spine with the use of two pairs of combs 5 and hooks 13 positioned at the ends of the rod 1, whereas in the children aged from 8 to 11 suffering from nonfixed forms of scoliosis, only one pair of combs 5 and 20 has been set at each end of the rod 1 without the use of the hooks 13.

When setting the correctant in three patients with an angle of curvature of the spine exceeding 50° according to Cobb, a pair 22 of combs 5 and 20 and hooks 13 has been positioned on each end of the rod 1, while the third pair 22 of the combs 5, 20 has been positioned at the vertex of the spinal curvature. A frame-type apparatus has been resorted to within the postoperative period, whereby the spine 2 has been finally tracted by Kirschner's pins till getting rectified completely, whereupon the frame-type apparatus has been removed, and further fixation of the spine has been carried out with the use of an implantable correctant.

In the patients suffering from scoliotic spinal curvature with an angle of curvature over 70° according to Cobb, first there have been implanted three pairs 22 of the combs 5, 20 with which the spine has been subjected to distraction and rectification in the frame-type apparatus, whereupon the correcting rod 1 has been implanted.

Each operation for inserting the correcting rod took from 1 to 3 hours depending on the degree of spinal curvature. All the patients operated upon tolerated the surgery well, the postoperative periods being uneventful and free from any complications. On the third or fourth day after the operation the patients were allowed to get up, while on the ninth or tenth day the sutures were removed and the patients were dismissed from the hospital. School-children resumed attending the school at the place of their residence. No resort was made to plaster-of-Paris or removable jackets.

What is claimed is:

1. An implantable correctant of a spinal curvature, comprising:
    a rod of a generally rectangular cross section, shaped in an arc, positioned on one side of the spinous processes with the convexity of the rod facing the convexity of the spine; and
    a tension fixation device mounted on the spine, said device straightening said rod and said spine to correct said spinal curvature.

2. An implantable correctant of a spinal curvature as claimed in claim 1, wherein at least one end of said rod is thicker than a central region of said rod, and a side surface of said end is bevelled.

3. An implantable correctant of a spinal curvature as claimed in claim 2, wherein said tension fixation device comprises:
    a first and a second comb situated at opposite ends of said rod on the spine and facing with their teeth towards said rod;
    cross braces in a number to suit the number of said combs, said cross braces being connected at one of their ends to a first means connected to said rod and the other ends of said cross braces connected to the respective comb.

4. An implantable correctant of a spinal curvature as claimed in claim 3, further comprising:
    an oblong longitudinal hole in one of said tapered ends of said rod;
    a screw of said tension fixation device, said screw being screwed in said oblong hole; and
    a cross brace mounted on said screw.

5. An implantable correctant of a spinal curvature as claimed in claim 2, wherein said tension fixation device comprises:
    at least one hook held near one end of said rod and inserted within a vertebral arch.

6. An implantable correctant of a spinal curvature as claimed in claim 5, wherein said tension fixation device comprises:

at least one hook held near the other end of said rod and inserted within a vertebral arch.

7. An implantable correctant of a spinal curvature as claimed in claim 5, comprising:
an oblong longitudinal hole in one of said tapered ends of said rod;
a screw of said tension fixation device, said screw being screwed in said oblong hole; and
a cross brace mounted on said screw.

8. An implantable correctant of a spinal curvature as claimed in claim 5, wherein said tension fixation device further comprises a compression fixation device, said compression fixation device comprising:
a pair of combs situated in the middle portion of said rod each on one side of the spinous processes so as to face each other with their teeth; and
a cross brace with one end of said cross brace held to said rod in the middle portion thereof, while the other end of said brace carries said combs.

9. An implantable correctant of a spinal curvature as claimed in claim 2, wherein said tension fixation device further comprises a compression fixation device, said compression fixation device comprises:
a pair of combs situated in the middle portion of said rod each on a different side of the spinous processes so as to face each other with their teeth;
a cross brace with one end of said cross brace held to said rod in the middle portion thereof, while the other end of said brace carries said combs.

10. An implantable correctant of spinal curvature as claimed in claim 1, wherein said tension fixation device comprises:
a first and a second comb situated at opposite ends of said rod, said combs positioned on the spine and facing with their teeth towards said rod;
cross braces in a number to suit the number of said combs, said cross braces being connected at one of their ends to a first means connected to said rod and the other end of said cross braces connected to said respective comb.

11. An implantable correctant of a spinal curvature as claimed in claim 10, wherein said tension fixation device comprises:
a third and a fourth comb interposed between said rod and the spine on the convexity thereof, each of said third and fourth combs facing the teeth of said first and second comb and being held respectively on said cross braces.

12. An implantable correctant of a spinal curvature as claimed in claim 11, wherein said tension fixation device further comprises:
at least one hook adjacent said rod is connected near an end of a second means to catch a vertebral arch.

13. An implantable correctant of a spinal curvature as claimed in claim 11, comprising:
an oblong longitudinal hole in one of said tapered ends of said rod;
a screw of said tension fixation device, said screw being screwed in said oblong hole; and
a cross brace mounted on said screw.

14. An implantable correctant of a spinal curvature as claimed in claim 11, wherein said tension fixation device comprises:
a pair of combs situated in the middle portion of said rod each on one side of the spinous processes so as to face each other with their teeth;
a cross brace with one end of said cross brace held to said rod in the middle portion thereof, while the other end of said brace carries said combs.

15. An implantable correctant of a spinal curvature as claimed in claim 10, wherein said tension fixation device comprises:
at least one hook adjacent said rod, connected near an end of a second means and adaptable to be inserted within a respective vertebral arch.

16. An implantable correctant of a spinal curvature as claimed in claim 10, comprising:
an oblong longitudinal hole in one of said tapered ends of said rod;
a screw of said tension fixation device, said screw being screwed in said oblong hole; and
a cross brace mounted on said screw.

17. An implantable correctant of a spinal curvature as claimed in claim 10, wherein said tension fixation device further comprises a compression fixation device, said compression fixation device comprises:
a pair of combs situated in the middle portion of said rod, each on one side of the spinous processes so as to face each other with their teeth;
a cross brace with one end of said cross brace held to said rod in the middle portion thereof, while the other end of said brace carries said combs.

18. An implantable correctant of a spinal curvature as claimed in claim 1, wherein said tension fixation device further comprises a compression fixation device, said compression fixation device comprises:
a pair of combs located in the middle portion of said rod, each on a different side of the spinous processes with their teeth facing one another;
a cross brace with one end of said cross brace held to said rod in the middle portion thereof, while the other end of said brace carries said combs.

19. A method for treatment of a spinal curvature using an implantable correctant made as an arc-shaped rod of generally rectangular cross section, comprising:
cutting an incision as long as the rod lengthwise of the spine on the convex side of its curvature,
exposing the vertebrae at the ends of the incision by separating them from the adjacent muscles,
positioning the rod with its convexity towards that of the spine and held with its ends to the spine using a fixation device so that the rod is straightened, thus building up a force for partially deflecting the spine in a direction opposite the initial curvature,
equalizing the size of osseous formations on the convexity and concavity of the spine; and
closing said incision when the rod has been fixed on the spine, applying the layer by layer techniques.

20. A method for treatment of a spinal curvature using an implantable correctant made as an arc-shaped rod of generally rectangular cross section, comprising:
making incisions in the thoracic and lumbar regions adjacent the spine on the convex side thereof,
exposing the vertebrae at the places of incisions by separating the adjacent muscles,
inserting the rod into the incision in the area of the lumbar spine, and then pushing said rod, using the enclosed technique and separating the soft tissues as the rod is advanced,
repositioning the rod with its convexity towards that of the spine and retaining the rod ends adjacent the spine using fixation devices so that the rod is straightened thus applying a force to straighten the spine; and
closing the incisions once the rod has been fixed on the spine, applying the layer by layer technique.

* * * * *